United States Patent [19] [11] Patent Number: 4,578,386
Lee [45] Date of Patent: Mar. 25, 1986

[54] 7,8-DIHYDROIMIDAZO[1,5-A]PYRAZIN-8-ONES

[75] Inventor: Thomas D. Lee, Scarsdale, N.Y.

[73] Assignee: USV Pharmaceutical Corp., Tarrytown, N.Y.

[21] Appl. No.: 578,916

[22] Filed: Feb. 10, 1984

[51] Int. Cl.⁴ .............. C07D 487/04; C07D 519/00; A61K 31/50; A61K 31/53
[52] U.S. Cl. .................. 514/241; 514/242; 514/245; 514/249; 544/105; 544/182; 544/216; 544/277; 544/295; 544/238; 544/350; 548/336; 548/337; 548/342; 548/309; 548/313; 548/315; 548/316; 548/318; 548/321; 548/322; 548/307
[58] Field of Search .............. 424/250, 251, 249; 544/350, 182, 216, 238, 277, 295, 182, 216; 514/242, 241, 245, 249

[56] References Cited
PUBLICATIONS
Abushanab et al., Chem. Abs. 83, 206205t (1975).

Primary Examiner—Mark L. Berch

[57] ABSTRACT

Provided are compounds of the structure:

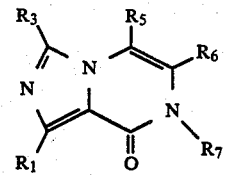

wherein
$R_1$, $R_3$, $R_5$ and $R_6$ are independently H, alkyl, aralkyl, aryl, substituted aryl, heteroaryl, substituted heteroaryl, alkenyl, alkynyl, hydroxy, hydroxyalkyl, alkoxy, mercapto, mercaptoalkyl, alkylthio, amino, alkylamino, aminoalkyl, formyl, carboxy and salts thereof, carbalkoxy, alkanoyl, cyano, nitro, halo, trifluoromethyl, alkylsulfonyl, aminosulfonyl, carbamoyl or cycloalkyl; and
$R_7$ is H, alkyl, aryl, aralkyl, oxo, or alkanoyl;
wherein at least one of $R_1$, $R_5$ or $R_6$ is an aryl, heteroaryl, or heteroaryl substituted with H, alkyl, halo, amino, trifluoromethyl or cyano.

19 Claims, No Drawings

7,8-DIHYDROIMIDAZO[1,5-A]PYRAZIN-8-ONES

The present invention relates to new organic compounds possessing valuable pharmacological activity. In particular, the invention relates to compounds of the structures:

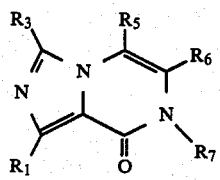

Formula I wherein $R_1$, $R_3$, $R_5$ and $R_6$ are independently H, alkyl, aralkyl, aryl, substituted aryl, heteroaryl, substituted heteroaryl, alkenyl, alkynyl, hydroxy, hydroxyalkyl, alkoxy, mercapto, mercaptoalkyl, alkylthio, amino, alkylamino, aminoalkyl, formyl, carboxy and salts thereof, carbalkoxy, alkanoyl, cyano, nitro, halo, trifluoromethyl, alkylsulfonyl, aminosulfonyl, carbamoyl or cycloalkyl; and $R_7$ is H, alkyl, aryl, aralkyl, oxo, or alkanoyl;

wherein at least one of $R_1$, $R_5$ or $R_6$ is aryl, a heteroaryl or heteroaryl substituted with H, alkyl, halo, amino, trifluoromethyl or cyano.

The alkyl groups in alkyl per se, hydroxyalkyl, alkoxy, aminoalkyl, alkylamino, alkylthio, mercaptoalkyl, alkanoyl, aralkyl, and carbalkoxy are preferably lower alkyl having from 1 to 8 carbon atoms, more preferably from 1 to 4 carbon atoms, and may be straight chain or branched. These groups include methyl, ethyl, propyl, isopropyl, sec-butyl, iso-amyl, hexyl, 2-ethylhexyl and the like.

The alkenyl and alkynyl groups may be straight chain or branched and preferably have 2 to 8 carbon atoms. These lr branched groups include vinyl, propenyl, ethynyl, propinyl and the like.

The preferred compounds are those wherein $R_1$ is H, $C_1$-$C_4$ alkyl, aryl, heteroaryl, carboxy or carbalkoxy; $R_3$ is H, $C_1$-$C_4$ alkyl, aryl, carboxy or carbalkoxy, halo, cyano, amino, hydroxy (keto form) or carbamoyl. When $R_3$ is hydroxy and exists as keto form, the N at the 2 position can be substituted with H, $C_1$-$C_4$ alkyl or $C_1$-$C_4$ alkanoyl. $R_5$ is preferably H, $C_1$-$C_4$ alkyl, aryl, halo, or trifluoromethyl. $R_6$ is preferably heteroaryl. $R_7$ is preferably H, $C_1$-$C_4$ alkyl, or $C_1$-$C_8$ alkanoyl.

Aryl includes phenyl and phenyl substituted with alkoxy, amino or halo.

Heteraryl preferably contains a nitrogen; and includes imidazole, pyrazole, pyrrole, triazine, pyridazine, pyrimidine, pyridine, pyrazine, purine, benzimidazole, indole, phthalazine, and quinoline.

It is more preferred that $R_6$ be a pyridyl. The nitrogen may be at any position. The para is preferred. The heteroaryl may be substituted; if so, preferably with halo or amino.

The compounds may be prepared by the following series of reactions.

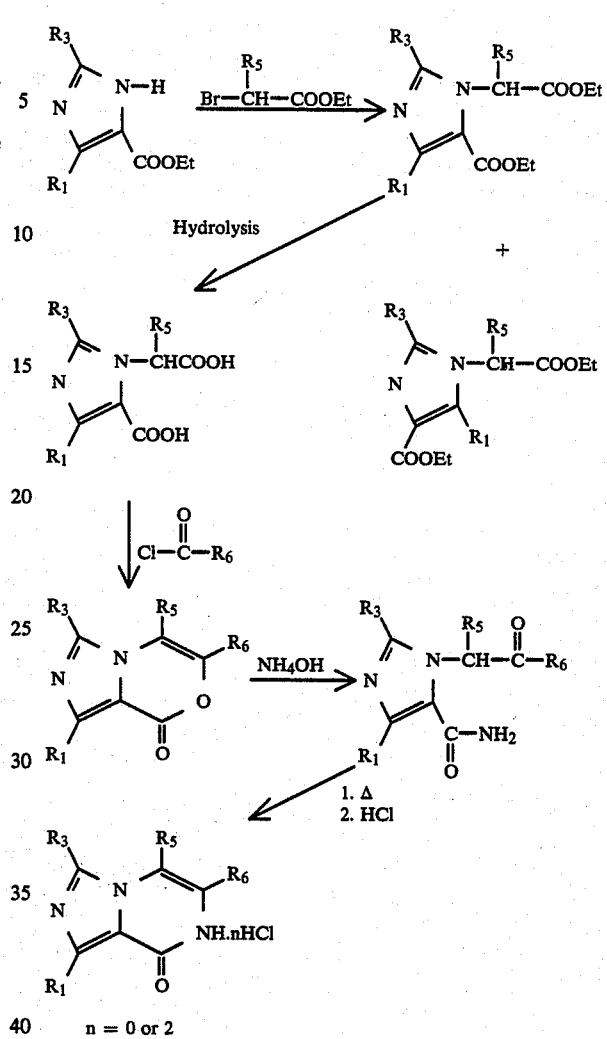

n = 0 or 2

Other standard reactions known to those skilled in the art, such as alkylation, halogenation, nucleophilic displacement reaction, hydrolysis, decarboxylation, etc., can be carried out to modify or introduce other functional groups.

The invention will be more fully understandable from the examples which follow. These examples are given by way of illustration and are not to be considered as limiting.

EXAMPLE 1

1A 1-α-Carbethoxyethyl-4-methylimidazole 5-carboxylic acid ester

With stirring, a mixture of ethyl 4-methyl-5-imidazole carboxylate (90 g), ethyl 2-bromopropionate (100 ml) and anhydrous potassium carbonate (300 g) in dimethylformamide (1 L) was heated for five hours. After filtration, the solvent was removed with reduced pressure and the residue was partitioned between chloroform and water. The organic layer was dried and concentrated to a dark oil which according to thin layer chromatography, was a mixture of two products. Separation by silica gel dry column gave the pure captioned product (78 g) as a brown oil.

1B. 1-α-Carboxyethyl-4-methylimidazole 5-carboxylic acid

The diester of 1A (40 g) was mixed with 200 ml of 5% aqueous sodium hydroxide and was heated on a steam bath overnight. After neutralization with hydrochloric acid, the mixture was first evaporated and then pumped to dryness. The brownish solid residue (44 g) thus obtained was used for the next step without purification.

1C. 1,5-Dimethyl-8-oxo-6-(4'-pyridyl)-8H-imidazo[5,1-c][1,4]-oxazine

The compound of 1B (44 g) and isonicotinoyl chloride (95 g) was well mixed in a round bottom flask. The mixture was heated in an oil bath from 140°–190° C. for 10 minutes. After cooling, it was treated with ice water, neutralized with base and extracted with chloroform. The organic layer was concentrated and then filtered through a short silica gel dry column. Evaporation of the chloroform elute followed by crystallization of the residue with acetonitrile furnished the product as yellowish prisms, 7 g, m.p. 189°–191° C.

1D. 1-α-Isonicotinoylethyl-4-methylimidazol 5-carboxamide

The compound of 1C (5.8 g) was treated with 40 ml of 28% ammonium hydroxide. The mixture was heated on a steam bath for 5 minutes to cause dissolution. As soon as the starting material dissolved, there was a white solid precipitating out. The reaction was heated for another 10 minutes and then filtered. The white solid was washed with hot water and then recrystallized from ethanol-chloroform to give 4.2 grams of product, m.p. 272°–273° C.

1E. 1,5-Dimethyl-8-oxo-6-(4'-pyridyl)-7,8-dihydroimidazo-[1,5-a]pyrazine dihydrochloride The compound of 1D (2.5 g) was treated with 50 ml of Dowtherm A and the mixture was refluxed for a short time. After cooling, it was filtered and the crude product collected was recrystallized twice from methanol-acetonitrile to give white needles, 1.5 g, m.p. >280° C.

Treatment of this base with methanolic-HCl followed by evaporation and recrystallization with methanol-acetonitrile, the dihydrochloride salt was obtained as yellowish needles, m.p. >280° C.

EXAMPLE 2

2A. 1-α-Carbethoxypentyl-4-methylimidazole 5-carboxylic acid ethyl ester

From a mixture of ethyl 4-methyl-5-imidazole carboxylate (65 g), α-bromohazanoate (105 g) and anhydrous potassium carbonate (120 g) in dimethylformamide (800 ml), a total of 38 grams of captioned product as a brown oil was prepared similarily as in Example 1A.

2B. 1-α-Carboxypentyl-4-methylimidazole 5-carboxylic acid

Prepared similarily as in Example 1B, 34 grams of product was obtained from 30 grams of 2A.

2C. 5-n-Butyl-1-methyl-8-oxo-6-(4'-pyridyl)-8H-imidazo[5,1-c][1,4]oxazine

Prepared similarily as in Example 1C, from the product of 2B (35 g) and isonicotinoyl chloride (50 g), a total of 5.7 grams of product as an orange colored solid was obtained, m.p. 119°–122° C.

The hydrochloride salt was prepared via treatment of the captioned product with $CH_2Cl_2$—HCl, m.p. 252° C. (dec).

2D. 1-α-Isonicotinoylpentyl-4-methylimidazole 5-carboxamide

Prepared similarily as in Example 1D as above, 1.5 grams of product as an orange colored solid was obtained from 1.6 grams of starting material from Example 2C.

2E. 5-n-Butyl-1-methyl-8-oxo-6-(4'-pyridyl)-7,8-dihydroimidazo-[1,5-a]pyrazine dihydrochloride Prepared similarly as in Example 1E, the free base product (0.5 g) as an off-white solid was obtained from the product of 2D (1.5 g), m.p. 246°–248° C. ($CH_3OH$—$CH_3CN$).

The dihydrochloride salt was also prepared similarly as cream colored prisms, m.p. 285° C. (dec) ($CH_3OH$).

Following the procedures in the above examples, the following additional compounds can be obtained.

EXAMPLE 3

1-Methyl-8-oxo-5-phenyl-6-(4'-pyridyl)-7,8-dihydroimidazo[1,5-a]pyrazine

EXAMPLE 4

5-Methyl-8-oxo-1-phenyl-6-(4'-pyridyl)-7,8-dihydroimidazo[1,5-a]pyrazine

EXAMPLE 5

1,6-Di(4'-pyridyl)-5-methyl-8-oxo-7,8-dihydroimidazo[1,5-a]pyrazine

EXAMPLE 6

1,5-Dimethyl-8-oxo-6-(3'-pyridyl)-7,8-dihydroimidazo[1,5-a]pyrazine

EXAMPLE 7

3-Bromo-1,5-dimethyl-8-oxo-6-(4'-pyridyl)-7,8-dihydroimidazo[1,5-a]pyrazine

EXAMPLE 8

3,8-Dioxo-1,5-dimethyl-6-(4'-pyridyl)-2,3,7,8-tetrahydroimidazo[1,5-a]pyrazine

EXAMPLE 9

5-n-Butyl-3,8-dioxo-1-methyl-6-(4'pyridyl)-2,3,7,8-tetrahydroimidazo[1,5-a]pyrazine

EXAMPLE 10

3-Amino-1,5-dimethyl-8-oxo-6-(4'-pyridyl)-7,8-dihydroimidazo[1,5-a]pyrazine

EXAMPLE 11

3-Cyano-1,5-dimethyl-8-oxo-6-(4'-pyridyl)-7,8-dihydroimidazo[1,5-a]pyrazine

EXAMPLE 12

1,5-Dimethyl-8-oxo-6-(4'-pyridyl)-7,8-dihydroimidazo[1,5-a]pyrazine 3-carboxylic acid Compounds of this invention may be useful for the treatment of congestive heart failure as can be demonstrated by their ability to pass a standard in vitro inotropic test. In this experiment, the test compound, dissolved in a vehicle, was applied on several strips of guinea pig left atria muscle. The change of the muscle tension versus the drug concentration was measured and the concentration which caused 25% increase of the muscle tension was calculated as the $EC_{25}$ value. The experiment was then repeated with muscle strips obtained from animals which had been pretreated with reserpine (therefore catecholamine was depeleted) prior to sacrifice. Positive results from both experiments indicate the test compound can directly increase the muscle contraction. Compounds of Examples 1 and 2 are both active inotropic agents showing $EC_{25}$ in isolated guinea pig left atria muscles of 86 $\mu$M and 24.9 $\mu$M respectively. This high activity is reproducible in reserpine pretreated preparations.

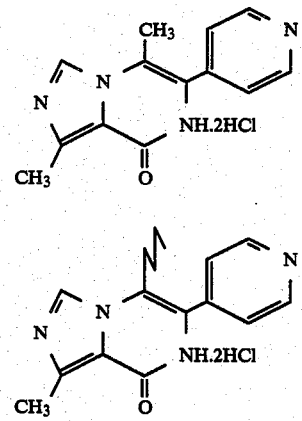

|  | EXAMPLE 1 % Increase from Control | | EXAMPLE 2 % Increase from Control | |
|---|---|---|---|---|
| Concentration | Normal | Reserpinized | Normal | Reserpinized |
| $10^{-4}$ M | 27 ± 5% | 29 ± 4% | 46% | 26 ± 8% |
| $10^{-3}$ M | 81 ± 8% | 80 ± 9% | 86% | 53 ± 15% |

The present invention includes within its scope a composition for treating congestive heart failure, said composition comprising a pharmaceutically acceptable carrier and, as the active component thereof, a compound of Formula I or pharmaceutically acceptable acid-addition salt thereof. The invention also includes within its scope the method for treating congestive heart failure in a patient requiring such treatment which comprises administering to such patient an effective amount of a compound of Formula I or pharmaceutically acceptable acid-addition salt thereof. In clinical practice said compound of salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc, and the like.

Liquid compositions for oral administration include pharmaceutically acceptable emulsions, solutions, suspensions, syrups and elixers containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegatable oils such as olive oil and injectable organic esters such as ethyl oleate. These compositions can also contain adjuvants such as stabilizing, preserving, wetting, emulsifying and dispersing agents.

They can be sterilized, for example, by filtration through a bacterial-retaining filter, by incorporation of sterilizing agents in the compositions, by irradiation or by heating. They can also be manufactured in the form of sterile solid compositions which can be dissolved in sterile water or some other sterile injectable medium immediately before use.

The percentages of active component in the said composition and method for treating congestive heart failure can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

What is claimed is:
1. Compounds of the formula

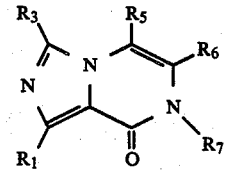

wherein
$R_1$, $R_3$, $R_5$ and $R_6$ are independently H; $C_1$–$C_8$ alkyl; ar $C_1$–$C_8$ alkyl; an aryl substituent which is phenyl or phenyl mono substituted with $C_1$–$C_8$ alkyl, halo, amino, trifluoromethyl or cyano; a heteroaryl substituent which is imidazole, pyrazole, pyrrole, triazine, pyridazine, pyrimidine, pyridine, pyrazine, purine, benzimidazole, indole, phthalazine, quinoline or the heteroaryl mono substituted with $C_1$–$C_8$ alkyl, halo, amino, trifluoromethyl or cyano; $C_2$–$C_8$ alkenyl; $C_2$–$C_8$ alkynyl; hydroxy, hydroxy-$C_1$–$C_8$ alkyl, $C_1$–$C_8$ alkoxy, mercapto, mercapto $C_1$–$C_8$ alkyl, $C_1$–$C_8$ alkythio, amino, $C_1$–$C_8$ alkylamino, amino $C_1$-$C_8$ alkyl, formyl, carboxy and salts thereof, $C_1$-$C_8$ carb alkoxy, $C_1$-$C_8$ alkanoyl, cyano, nitro, halo, trifluoromethyl, $C_1$-$C_8$ alkylsulfonyl, aminosulfonyl, carbamoyl or $C_3$-$C_8$ cycloalkyl;

$R_7$ is H, $C_1$-$C_8$ alkyl, an aryl substituent which is phenyl or phenyl mono substituted with alkoxy, amino or halo, ar $C_1$-$C_8$ alkyl, or $C_1$-$C_8$ alkanoyl;

wherein at least one of $R_1$, $R_5$ and $R_6$ is an aryl or heteroaryl, and pharmaceutically acceptable acid addition salts thereof.

2. A compound of claim 1 wherein $R_1$ is H, $C_1$-$C_4$ alkyl, aryl, heteroaryl, carboxy or carbalkoxy;

$R_3$ is H, $C_1$-$C_4$ alkyl, aryl, carboxy, carbalkoxy, halo, cyano, amino, hydroxy (keto form) or carbamoyl;

$R_5$ is H, $C_1$-$C_4$ alkyl, aryl, halo, or trifluoromethyl;

$R_6$ is a heteroaryl; and $R_7$ is H, lower $C_1$-$C_4$ alkyl or $C_1$-$C_4$ alkanoyl.

3. A method of treating congestive heart failure in a patient requiring such treatment, wherein the method comprises the administration of a composition containing effective amount of a compound of claim 1.

4. A compound of claim 2 wherein $R_3$ is H, halo, hydroxy (keto form), amino, cyano or carboxy, $R_5$ is $C_1$-$C_4$ alkyl or phenyl, $R_7$ is H, and $R_6$ is pyridyl.

5. A compound of claim 2 wherein $R_6$ is pyridyl.

6. A compound of claim 1 wherein the compound is 1,5-Dimethyl-8-oxo-6-(4'-pyridyl)-7,8-dihydroimidazo-[1,5-a]pyrazine and its pharmaceutically acceptable salts.

7. A compound of claim 1 wherein the compound is 5-n-Butyl-1-methyl-8-oxo-6-(4'pyridyl)-7,8-dihydroimidazo-[1,5-a]pyrazine and its pharmaceutically acceptable salts.

8. A compound of claim 1 wherein the compound is 1-Methyl-8-oxo-5-phenyl-6-(4'-pyridyl)-7,8-dihydroimidazo-[1,5a]pyrazine and its pharmaceutically acceptable salts.

9. A compound of claim 1 wherein the compound is 5-Methyl-8-oxo-1-phenyl-6-(4'-pyridyl)-7,8-dihydroimidazo[1,5-a]pyrazine and its pharmaceutically acceptable salts.

10. A compound of claim 1 wherein the compound is 1,6-Di(4'pyridyl)-5-methyl-7,8-dihydroimidazo[1,5-a]pyrazine and its pharmaceutically acceptable salts.

11. A compound of claim 1 wherein the compound is 1,5-Dimethyl-8-oxo-6-(3'-pyridyl)-7,8-dihydroimidazo-[1,5-a]pyrazine and its pharmaceutically acceptable salts.

12. A compound of claim 1 wherein the compound is 3-Bromo-1,5-dimethyl-8-oxo-6-(4'-pyridyl)-7,8-dihydroimidazo[1,5-a]pyrazine and its pharmaceutically acceptable salts.

13. A compound of claim 1 wherein the compound is 3,8-Dioxo-1,5-dimethyl-6-(4'-pyridyl)-2,3,7,8-tetrahydroimidazo[1,5-a]pyrazine and its pharmaceutically acceptable salts.

14. A compound of claim 1 wherein the compound is 5-n-Butyl-3,8-dioxo-1-methyl-6-(4'-pyridyl)-2,3,7,8-tetrahydroimidazo-[1,5-a]pyrazine and its pharmaceutically acceptable salts.

15. A compound of claim 1 wherein the compound is 3-Amino-1,5-dimethyl-8-oxo-6-(4'-pyridyl)-7,8-dihydroimidazo[1,5-a]pyrazine and its pharmaceutically acceptable salts.

16. A compound of claim 1 wherein the compound is 1,5-Dimethyl-8-oxo-6-(4'pyridyl)-7,8-dihydroimidazo[1,5-a]pyrazine and its pharmaceutically acceptable salts.

17. A compound of claim 1 wherein the compound is 1,5-Dimethyl-8-oxo-6-(4'pyridyl)-7,8-dihydroimidazo[1,5-a]pyrazine 3-carboxylic acid and its ester.

18. A pharmaceutical composition for treatment of congestive heart failure, said composition comprising a compound of claim 1 and a pharmaceutically acceptable carrier in an effective amount for treatment of congestive heart failure.

19. A pharmaceutical composition for treatment of congestive heart failure, said composition comprising a compound of claim 4 and a pharmaceutically acceptable carrier in an effective amount for treatment of congestive heart failure.

* * * * *